United States Patent
Gerlitz

(10) Patent No.: US 7,308,293 B2
(45) Date of Patent: Dec. 11, 2007

(54) NON-INVASIVE GLUCOSE METER

(75) Inventor: Jonathan Gerlitz, Petach Tikva (IL)

(73) Assignee: GlucoVista, LLC, Fairfield, NJ (US)

( * ) Notice: Subject to any disclaimer, the term of this patent is extended or adjusted under 35 U.S.C. 154(b) by 307 days.

(21) Appl. No.: 10/485,876

(22) PCT Filed: Aug. 1, 2002

(86) PCT No.: PCT/IB02/03774

§ 371 (c)(1),
(2), (4) Date: Aug. 12, 2004

(87) PCT Pub. No.: WO03/012486

PCT Pub. Date: Feb. 13, 2003

(65) Prior Publication Data

US 2004/0260159 A1    Dec. 23, 2004

(51) Int. Cl.
*A61B 5/00* (2006.01)
(52) U.S. Cl. ................... 600/318; 600/319
(58) Field of Classification Search ........... 600/318, 600/319, 320, 321
See application file for complete search history.

(56) References Cited

U.S. PATENT DOCUMENTS

| | | | |
|---|---|---|---|
| 3,958,560 A | 5/1976 | March | |
| 4,014,321 A | 3/1977 | March | |
| 4,877,322 A | 10/1989 | Hill | |
| 5,222,496 A * | 6/1993 | Clarke et al. | 600/316 |
| 5,318,022 A | 6/1994 | Taboada et al. | |
| 5,433,197 A | 7/1995 | Stark | |
| 5,523,883 A * | 6/1996 | Myers et al. | 359/629 |
| 5,560,356 A | 10/1996 | Peyman | |
| 5,743,262 A * | 4/1998 | Lepper et al. | 600/316 |
| 5,774,213 A | 6/1998 | Trebino et al. | |
| 5,776,060 A | 7/1998 | Smith et al. | |
| 5,820,557 A | 10/1998 | Hattori et al. | |
| 5,882,301 A | 3/1999 | Yoshida | |
| 5,885,224 A | 3/1999 | Yoshida | |
| 6,134,458 A * | 10/2000 | Rosenthal | 600/310 |
| 6,181,957 B1 | 1/2001 | Lambert et al. | |
| 6,305,804 B1 | 10/2001 | Rice et al. | |
| 6,424,850 B1 | 7/2002 | Lambert et al. | |
| 6,477,394 B2 | 11/2002 | Rice et al. | |
| 6,494,576 B1 | 12/2002 | L'Esperance, Jr. | |

(Continued)

FOREIGN PATENT DOCUMENTS

WO    PCT/IB02/03774    8/2002

*Primary Examiner*—Eric Winakur
*Assistant Examiner*—Etsub D Berhanu
(74) *Attorney, Agent, or Firm*—Knobbe Martens Olson & Bear LLP

(57) ABSTRACT

An apparatus for measuring a concentration of a substance in an eye (13) includes a measurement light source (4) producing a measurement light beam having a first wavelength at which the substance has a non-zero first absorption coefficient. The apparatus further includes a reference light source (6) producing a reference light beam having a second wavelength at which the substance has a second absorption coefficient which is substantially equal to zero. At least a portion of the measurement light beam retro-reflects from the retina (17) and at least a portion of the reference light beam retro-reflects from the retina (17). The apparatus further includes a detector (9) responsive to light having the first wavelength by generating a measurement signal and responsive to light having the second wavelength by generating a reference signal.

23 Claims, 3 Drawing Sheets

U.S. PATENT DOCUMENTS

| | | |
|---|---|---|
| 6,574,501 B2 | 6/2003 | Lambert et al. |
| 6,853,854 B1 | 2/2005 | Proniewicz et al. |
| 6,895,264 B2 | 5/2005 | Rice et al. |
| 6,958,039 B2 | 10/2005 | Burd et al. |
| 6,968,222 B2 | 11/2005 | Burd et al. |
| 6,975,892 B2 | 12/2005 | Burd et al. |
| 6,998,247 B2 | 2/2006 | Monfre et al. |
| 7,039,446 B2 | 5/2006 | Ruchti et al. |
| 2002/0049389 A1 | 4/2002 | Abreu |

* cited by examiner

NON-INVASIVE GLUCOSE METER

BACKGROUND OF THE INVENTION

Numerous systems were suggested in the last decades, to solve the problem of a Non-Invasive Glucose-Meter.

The main drawback of all those systems was a very poor signal to noise ratio, which required a very heavy computing system, and resulted in inconsistent and unrepeatable results.

SUMMARY OF THE INVENTION

According to one aspect of embodiments of the present invention, a method determines the concentration of a substance in an eye. The eye has a cornea, a pupil, an iris, a lens, a liquid, and a retina. The method comprises providing a measurement light beam having a first wavelength at which the substance has a non-zero first absorption coefficient. The method further comprises providing a reference light beam having a second wavelength at which the substance has a second absorption coefficient which is substantially equal to zero. The method further comprises irradiating the retina with the measurement light beam, thereby passing the measurement light beam through the cornea, the pupil, the lens, and the liquid. The method further comprises irradiating the retina with the reference light beam, thereby passing the reference light beam through the cornea, the pupil, the lens, and the liquid. The method further comprises reflecting at least a portion of the measurement light beam from the retina and through the liquid, the lens, the pupil, and the cornea, thereby producing a measurement retro-reflected light beam having the first wavelength. The method further comprises reflecting at least a portion of the reference light beam from the retina and through the liquid, the lens, the pupil, and the cornea, thereby producing a reference retro-reflected light beam having the second wavelength. The method further comprises providing a detector adapted to generate a measurement signal in response to being irradiated by light having the first wavelength and to generate a reference signal in response to being irradiated by light having the second wavelength. The method further comprises irradiating the detector with the measurement retro-reflected light beam. The method further comprises irradiating the detector with the reference retro-reflected light beam. The method further comprises determining the concentration of the substance in the eye in response to the measurement signal and the reference signal from the detector.

In another aspect of embodiments of the present invention, an apparatus measures a concentration of a substance in an eye having a retina. The apparatus comprises a measurement light source producing a measurement light beam having a first wavelength. The substance has a non-zero first absorption coefficient for light at the first wavelength. The apparatus further comprises a reference light source producing a reference light beam having a second wavelength. The substance has a second absorption coefficient which is substantially equal to zero for light at the second wavelength. The apparatus further comprises an optical combiner comprising a dichroic coating layer. The optical combiner is positionable so that at least a portion of the measurement light beam retro-reflects from the retina and so that at least a portion of the reference light beam retro-reflects from the retina. The apparatus further comprises a detector positionable to receive the retro-reflected measurement light beam and the retro-reflected reference light beam. The detector is responsive to light having the first wavelength by generating a measurement signal and is responsive to light having the second wavelength by generating a reference signal. The apparatus further comprises an electrical circuit coupled to the detector. The electrical circuit is responsive to the measurement signal and the reference signal to measure the concentration of the substance in the eye.

DETAILED DESCRIPTION OF THE PREFERRED EMBODIMENT

Figure 1:
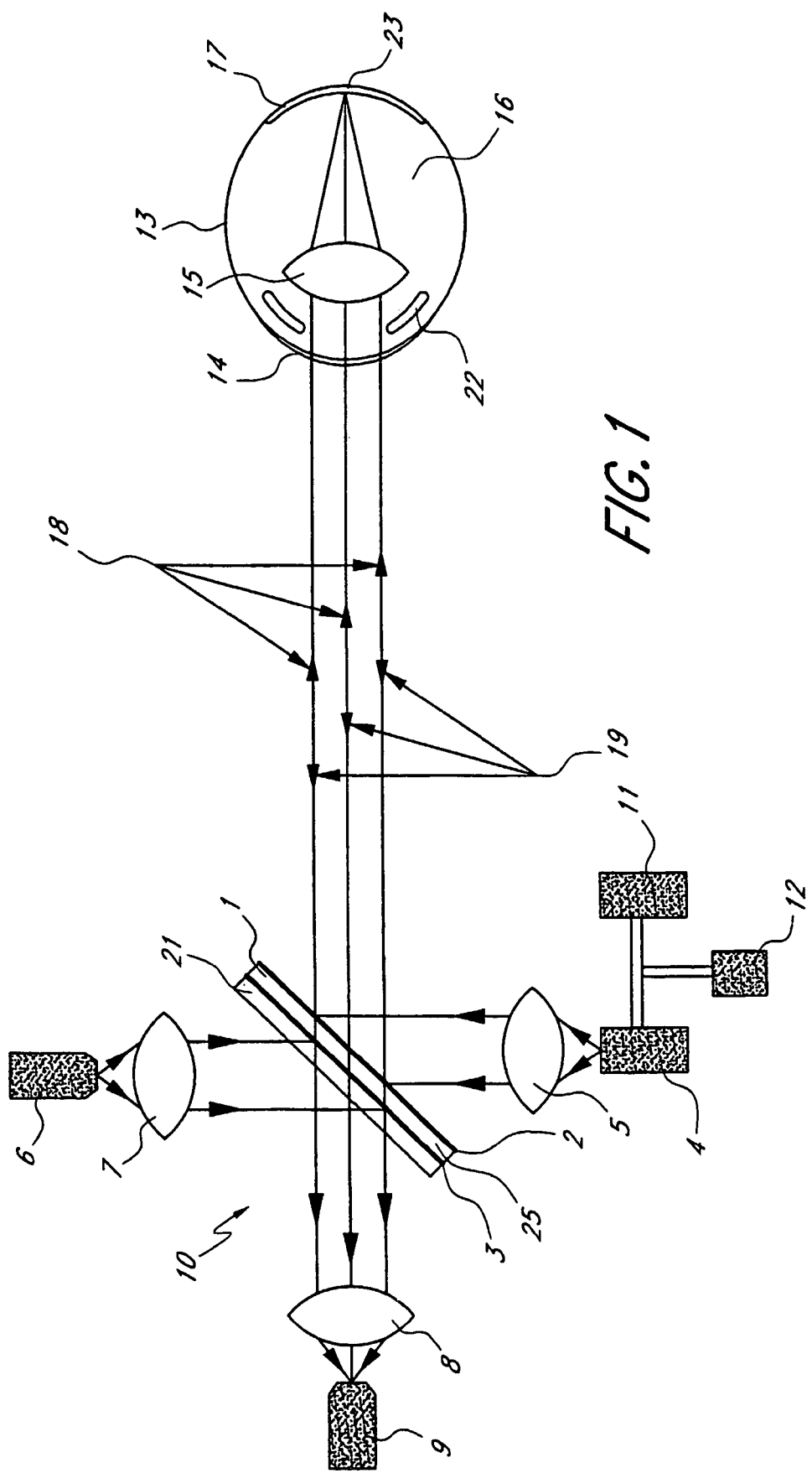
FIG. 1 schematically illustrates the principle of the Electro-Optic construction of the Non-Invasive Glucose-Meter in accordance with the preferred embodiment.

It is one objective of embodiments of the present invention to provide a Non-Invasive Glucose-Meter, which has a good signal to noise ratio, thus making the measurement consistent, repeatable and reliable.

It is another objective of embodiments of the present invention to provide such an apparatus for non-invasive glucose measurement, which is easy and simple to handle by the user, small sized and inexpensive.

It is a further objective of embodiments of the present invention to provide a Non-Invasive Glucose-Meter, which can be used in various environments, indoors and outdoors.

The objectives of embodiments of this invention can be achieved by using the properties of the eye as an optical apparatus. Every optical apparatus, which is equipped with focusing means and a focal plane, shows the phenomenon of retro-reflection, meaning: reflects back the entering light beam in the same direction it comes from. Embodiments of the current invention suggests an Electro-Optical apparatus which uses the retro-reflection characteristic of the eye in order to determine glucose or other substance concentration in the eye liquid (the vitreous body).

Certain embodiments of the apparatus has at least two infrared (IR) emitters to emit two different wavelength bands in the direction of the eye. Other embodiments emit the two different wavelength bands by using one wide band emitter and two narrow band filters. One of the wave bands is located in a wavelength where the glucose has a high absorption coefficient, the other wavelength is used for reference. The use of a reference beam compensates for changes of the iris, thus enables the use of the system in various light conditions.

An IR detector is located on the same optical path as the emitter, using a beam splitter (optical combiner), and thus, the retro-reflected beam from the eye returns towards the detector.

The retro-reflected beam passes twice throughout the eye, first through the cornea, the eye lens and liquid (vitreous body), then focuses on the retina and subsequently is reflected back through the eye liquid, lens and cornea towards the detector. Due to the long optical path in the eye, the absorption signal, which correlates to the exponential of $(\alpha_\lambda x)$, will be significant even in a low concentration of glucose.

The magnitude of the absorption is proportional to $$\int_{\lambda 1}^{\lambda 2} e^{\alpha_\lambda x} d\lambda$$

where x is the length of the optical path through the absorbing medium and $\alpha_\lambda$ is the absorption coefficient of the glucose at wavelength $\lambda$.

By using the retro-reflected light from the eye, which travels through a long optical path in the absorbing medium, certain embodiments of the current invention overcome the main drawback of all previous suggested systems, and inherently has a good signal to noise ratio. The optical system is quite simple, as described in the preferred embodiment, and due to the good signal to noise ratio, the processing of the signal is also simple and inexpensive.

FIG. 1 schematically illustrates the principle of the Electro-Optical construction of the Non-Invasive Glucose-Meter, in accordance with the preferred embodiment of the invention. An optical combiner 1 is located in the center of the system 10. The optical combiner 1 is made of four layers: dichroic coating 2, optical glass 25, holographic beam splitter 3, and cover glass 21. The dichroic coating 2, applied on one surface of optical glass 25, has a center wavelength, corresponding to the wavelength of a light source 4. Light sources 4, 6 and 11 are preferably laser diodes, or high power infrared light emitting diodes. The dichroic coating 2 enables 50-60% of the IR beam to pass through, and 40-50% of the IR beam to be reflected at a 90° angle towards the eye 13.

On the other surface of the optical glass 25 of the optical combiner 1, there is an holographic beam splitter 3, which has a center wavelength, corresponding to the wavelength of a light source 6. The holographic beam splitter allows 50-60% of the light beam of the center wavelength to pass through, and 40-50% of the light beam to be reflected at a 270° angle towards the eye 13. The light beams 18 of the two light sources are nearly parallel beams, created by using lenses 5 and 7. The light beams 18 are on the same optical path, and have, preferably, a diameter of about 2 mm.

The light beams 18 pass through the cornea 14, enter the iris 22, the eye lens 15 and the eye liquid 16, and focus approximately on the retina 17, at focal point 23. Part of the beam is reflected from the retina 17, and since it comes out of the same focal point 23, it will come out from the eye on the exact optical path of beams 18, but in the opposite direction, and is described by beam 19, propagating in the direction of the optical combiner 1. The beam passes the eye twice, thus the optical path in the absorbing medium is long, and the absorption signal correlates to the exponential of $(\alpha_\lambda x)$, will be much stronger than in any other suggested method. 50-60% of beam 19 passes through the beam splitter 3, focuses by means of lens 8 on an IR detector 9. The detector can be a silicon detector or PbS detector, or any other kind of IR detector known in the art.

The system 10 should be, preferably, located at a distance of at least 100 mm from the eye, in order to receive mainly the retro-reflected beam 19, and not other reflections, from the cornea for example, which are considered by the system 10 to be noise.

An alternative construction of the optical combiner 1, can be an optical combiner with only a dichroic coating 2. In this method, two light sources, 4 and 11, change position to emit the light beams intermittently, by using motor 12. In this variation, dichroic coating 2 is a wide band coating for both wavelengths of light sources 4 and 11.

Figure 2:
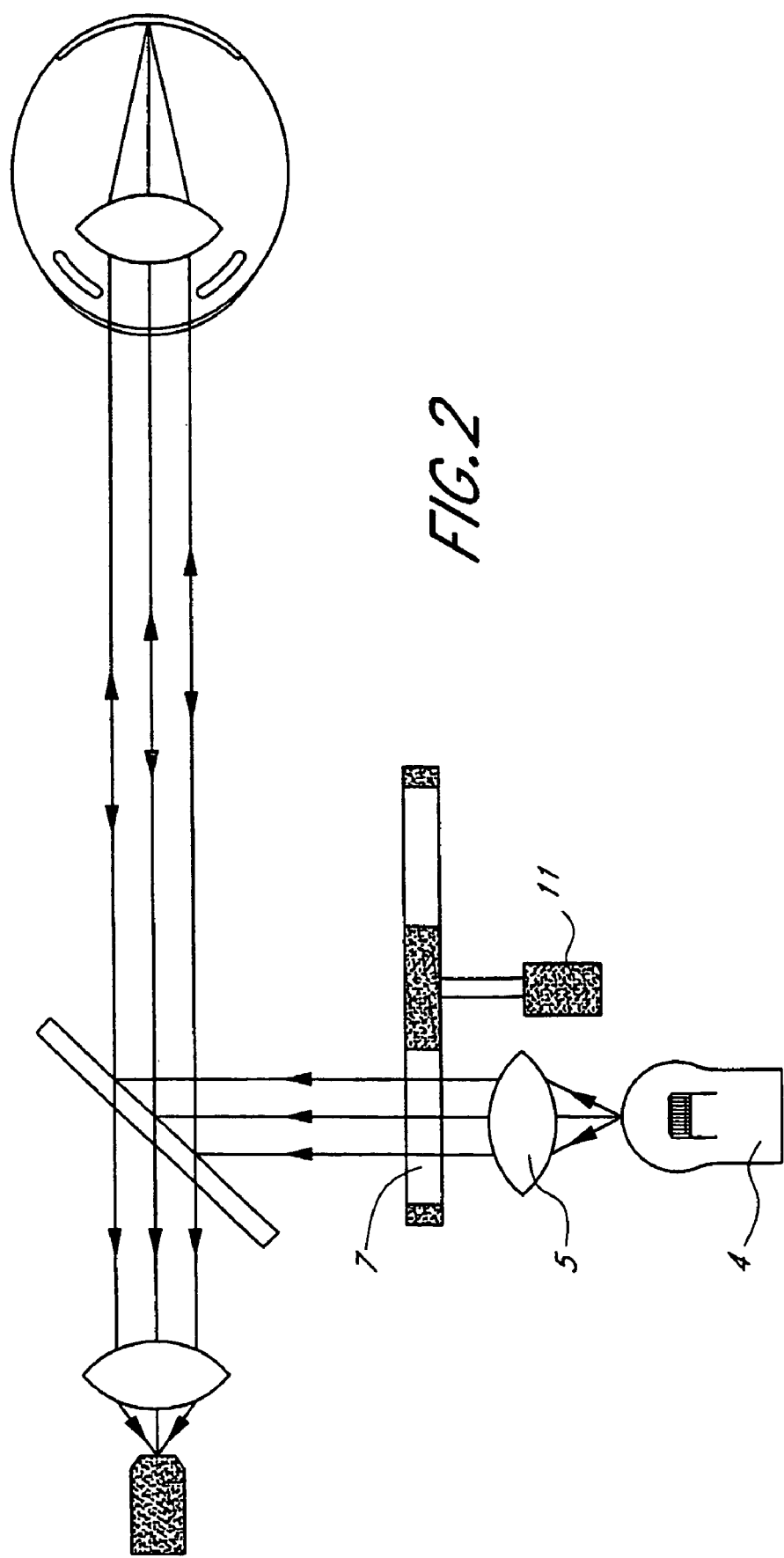
FIG. 2 schematically illustrates the principal of the Electro-Optic construction of the Non-Invasive Glucose-Meter in accordance with another embodiment.

FIG. 2 schematically illustrates the principle of the Electro-Optical construction of the Non-Invasive Glucose-Meter, in accordance with another embodiment of the present invention. In this embodiment, only one wide band light source 4 is used, which can be a miniature lamp. A filter wheel 7, driven by motor 11, is used to choose the required wavelengths. This embodiment is advantageous in case that more than two wavelengths are required in order to analyze glucose or other substances concentration.

Figure 3:
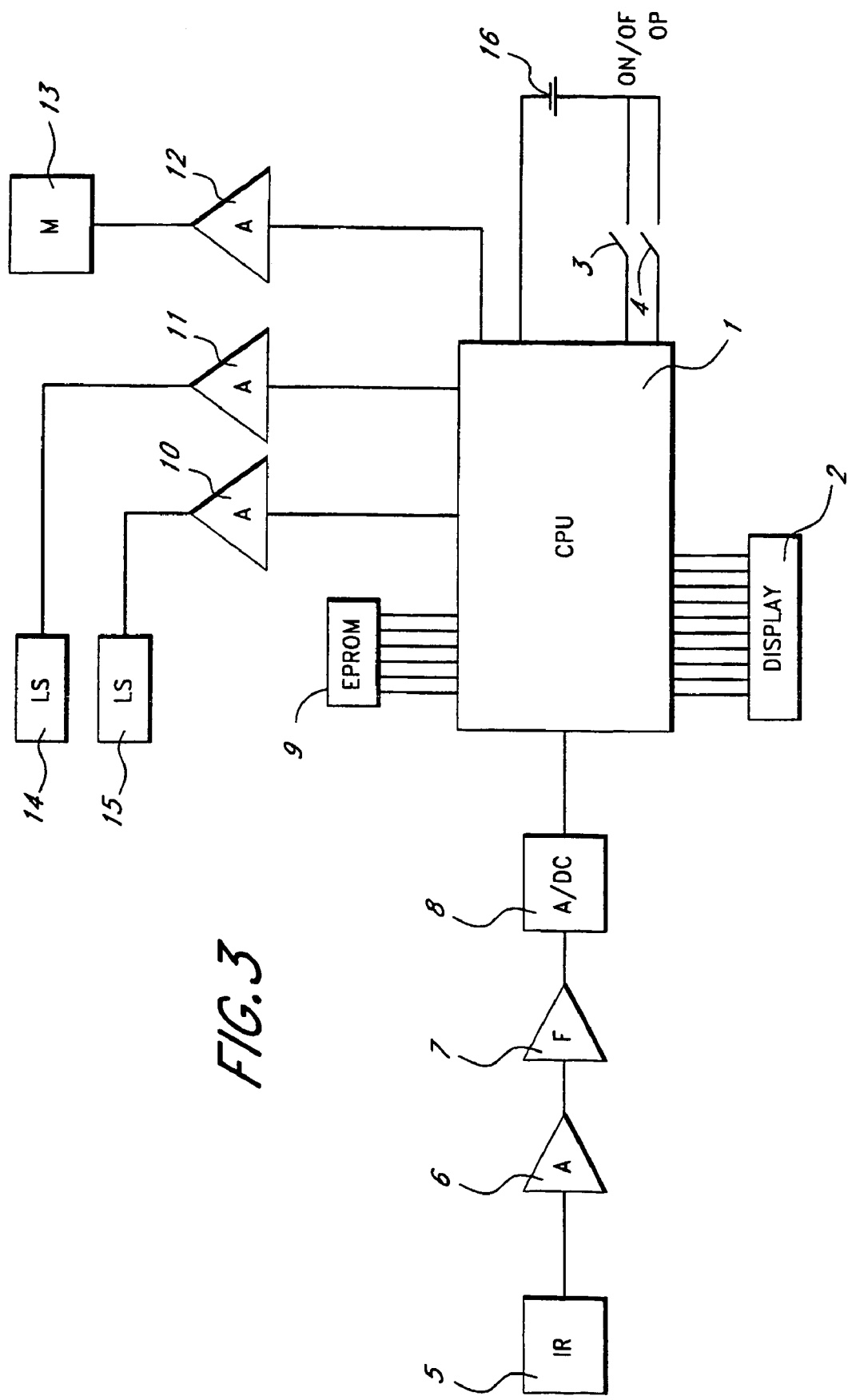
FIG. 3 schematically illustrates the electronic circuit, associated with the preferred embodiment.

FIG. 3 schematically illustrates the electronic circuit, associated with the preferred embodiment of the present invention. A central processing unit (CPU) 1, as Epson 6200, produced by Epson, Japan, controls the operation of the system.

The circuit is turned on by switch 3, connecting power source 16, preferably a Lithium battery, to the circuit. After a self-check, the CPU displays "Ready" on a display unit 2, such as a liquid crystal display (LCD). To perform a measurement, switch 4 is activated. Then, the CPU starts a measurement procedure. It activates in sequence light source 15 through amplifier 10 and light source 14 through amplifier 11, and activates motor 13 through amplifier 12 in the alternative embodiment. The retro-reflected light signal from the eye, is translated by IR detector 5 to a voltage signal, which is amplified by amplifier 6, and filtered by filter 7. The analog signal is converted to a digital form by an Analog to Digital (A/D) converter 8 and is stored by the CPU. After receiving measurement data corresponding to the two wavelengths, the CPU calculates the concentration of the glucose according to the absorption level, using calibration parameters stored in the $E^2$PROM 9. The result is display on display 2.

The same construction can be used to measure concentrations of other substances in the eye liquid, using other wavelengths.

Although the invention has been described in terms of certain preferred embodiments, other embodiments that are apparent to those of ordinary skill in the art, including embodiments which do not provide all of the features and advantages set forth herein, are also within the scope of this invention. Accordingly, the scope of the invention is defined by the claims that follow.

What is claimed is:

1. A method of determining the concentration of a substance in an eye, the eye having a cornea, a pupil, an iris, a lens, a liquid, and a retina, the method comprising:
   providing a nearly parallel measurement light beam having a first wavelength at which the substance has a non-zero first absorption coefficient;
   providing a nearly parallel reference light beam having a second wavelength at which the substance has a second absorption coefficient which is substantially equal to zero;
   irradiating the retina with the measurement light beam, thereby passing the measurement light beam through the cornea, the pupil, the lens, and the liquid;
   irradiating the retina with the reference light beam, thereby passing the reference light beam through the cornea, the pupil, the lens, and the liquid;
   reflecting at least a portion of the measurement light beam from the retina and through the liquid, the lens, the pupil, and the cornea, thereby producing a measurement retro-reflected light beam having the first wavelength;

reflecting at least a portion of the reference light beam from the retina and through the liquid, the lens, the pupil, and the cornea, thereby producing a reference retro-reflected light beam having the second wavelength;

providing a detector adapted to generate a measurement signal in response to being irradiated by light having the first wavelength and to generate a reference signal in response to being irradiated by light having the second wavelength, the detector located at a distance of at least 100 mm from the eye;

irradiating the detector with the measurement retro-reflected light beam;

irradiating the detector with the reference retro-reflected light beam; and determining the concentration of the substance in the eye in response to the measurement signal and the reference signal from the detector.

2. The method of claim 1, wherein the substance comprises glucose.

3. The method of claim 1, wherein the measurement light beam is provided by a first infrared light source and the reference light beam is provided by a second infrared light source.

4. The method of claim 3, wherein the first infrared light source comprises a laser diode or an infrared light emitting diode.

5. The method of claim 3, wherein the second infrared light source comprises a laser diode or an infrared light emitting diode.

6. The method of claim 1, wherein the measurement light beam is provided by a wideband light source and the reference light beam is provided by the wideband light source.

7. The method of claim 6, wherein the measurement light beam is transmitted through a first band filter and the reference light beam is transmitted through a second band filter.

8. The method of claim 1, wherein the measurement light beam and the measurement retro-reflected light beam are substantially parallel, and the reference light beam and the reference retro-reflected light beam are substantially parallel.

9. The method of claim 1, wherein the measurement light beam is focused at a point on the retina.

10. The method of claim 1, wherein the reference light beam is focused at a point on the retina.

11. An apparatus for measuring a concentration of a substance in an eye having a retina, the apparatus comprising:

a measurement light source producing a nearly parallel measurement light beam having a first wavelength, the substance having a non-zero first absorption coefficient for light at the first wavelength;

a reference light source producing a nearly parallel reference light beam having a second wavelength, the substance having a second absorption coefficient which is substantially equal to zero for light at the second wavelength;

an optical combiner comprising a dichroic coating layer, the optical combiner positionable so that at least a portion of the measurement light beam retro-reflects from the retina and so that at least a portion of the reference light beam retro-reflects from the retina;

a detector positionable to receive the retro-reflected measurement light beam and the retro-reflected reference light beam while the detector is located at a distance of at least 100 mm from the eye, the detector responsive to light having the first wavelength by generating a measurement signal and responsive to light having the second wavelength by generating a reference signal; and an electrical circuit coupled to the detector, the electrical circuit responsive to the measurement signal and the reference signal to measure the concentration of the substance in the eye.

12. The apparatus of claim 11, wherein the substance comprises glucose.

13. The apparatus of claim 11, wherein the optical combiner further comprises an optical glass layer, a holographic beam splitter layer, and a cover glass layer.

14. The apparatus of claim 11, further comprising a motor coupled to the measurement light source and the reference light source.

15. The apparatus of claim 11, wherein the measurement light source comprises a first infrared light source and the reference light beam comprises a second infrared light source.

16. The apparatus of claim 15, wherein the first infrared light source comprises a laser diode or an infrared light emitting diode.

17. The apparatus of claim 15, wherein the second infrared light source comprises a laser diode or an infrared light emitting diode.

18. The apparatus of claim 11, wherein the measurement light source comprises a wideband light source and the reference light source comprises the wideband light source.

19. The apparatus of claim 18, wherein the measurement light beam is transmitted through a first band filter and the reference light beam is transmitted through a second band filter.

20. The apparatus of claim 11, wherein the measurement light beam is substantially parallel to the retro-reflected measurement light beam, and the reference light beam is substantially parallel to the retro-reflected reference light beam.

21. The apparatus of claim 11, wherein the electrical circuit comprises a central processing unit (CPU), memory, and a display.

22. The apparatus of claim 11, wherein the electrical circuit is further coupled to the measurement light source and the reference light source.

23. An apparatus for measuring a concentration of a substance in an eye, the eye having a cornea, a pupil, an iris, a lens, a liquid, and a retina, the apparatus comprising:

means for providing a nearly parallel measurement light beam having a first wavelength at which the substance has a non-zero first absorption coefficient;

means for providing a nearly parallel reference light beam having a second wavelength at which the substance has a second absorption coefficient which is substantially equal to zero;

means for irradiating the retina with the measurement light beam, thereby passing the measurement light beam through the cornea, the pupil, the lens, and the liquid, wherein at least a portion of the measurement light beam is reflected from the retina and through the liquid, the lens, the pupil, and the cornea, thereby producing a measurement retro-reflected light beam having the first wavelength;

means for irradiating the retina with the reference light beam, thereby passing the reference light beam through the cornea, the pupil, the lens, and the liquid, wherein at least a portion of the reference light beam is reflected from the retina and through the liquid, the lens, the pupil, and the cornea, thereby producing a reference retro-reflected light beam having the second wavelength;

means for generating a measurement signal in response to the measurement retro-reflected light beam and for generating a reference signal in response to the reference retro-reflected light beam while the generating means is located at a distance of at least 100 mm from the eye; and means for determining the concentration of the substance in the eye in response to the measurement signal and the reference signal.

* * * * *